United States Patent [19]

Storey

[11] 4,061,128
[45] Dec. 6, 1977

[54] HAND-WARMING AND LIQUID-HEATING DEVICE

[76] Inventor: Curtis B. Storey, Box 290, Rte. 1, Limerick, Maine 04048

[21] Appl. No.: 697,855

[22] Filed: June 21, 1976

[51] Int. Cl.² .............................................. A61F 7/06
[52] U.S. Cl. .................................... 126/210; 126/265
[58] Field of Search ............... 126/208, 210, 261, 265; 219/279, 437, 523

[56] References Cited

U.S. PATENT DOCUMENTS

| 2,715,400 | 8/1955 | Butler | 126/208 |
| 3,220,541 | 11/1965 | Wei | 126/261 |
| 3,237,608 | 3/1966 | Brandl | 219/279 |
| 3,804,076 | 4/1974 | Fant et al. | 126/265 |

FOREIGN PATENT DOCUMENTS

| 163,918 | 6/1921 | United Kingdom | 126/261 |

Primary Examiner—John J. Camby
Assistant Examiner—Larry I. Schwartz
Attorney, Agent, or Firm—William Nitkin

[57] ABSTRACT

A hand-warming and liquid-heating unit comprising a catalytic heater with a liquid-containing chamber removably affixed thereon with means to open said chamber and, in an additional embodiment, auxiliary heating means for temperature regulation of said liquid.

7 Claims, 8 Drawing Figures

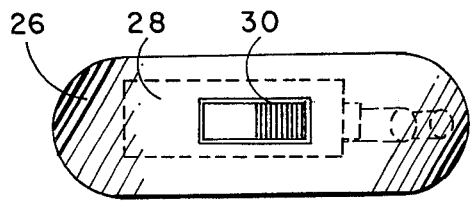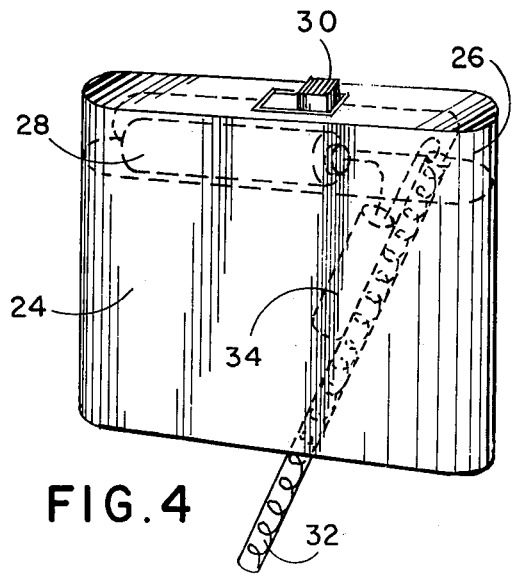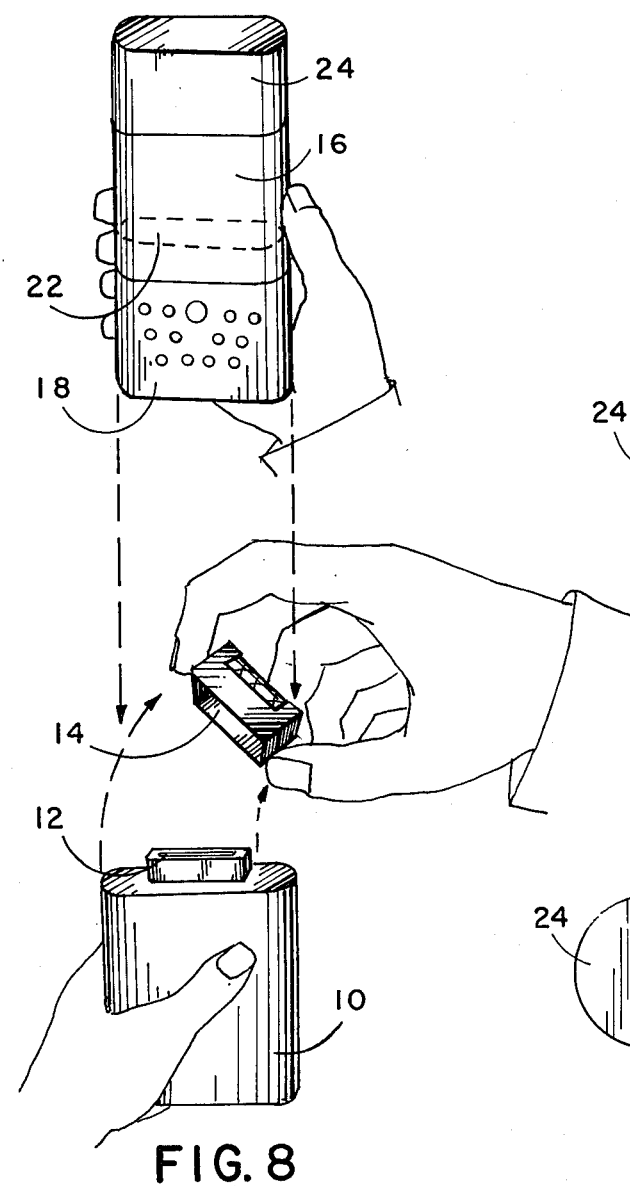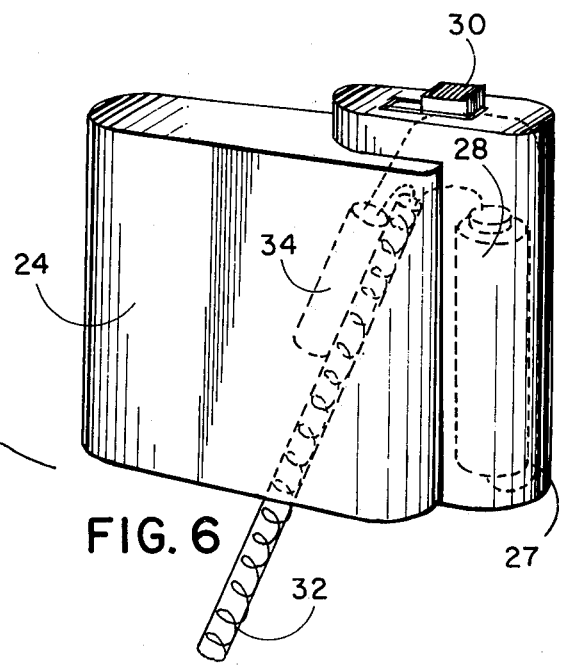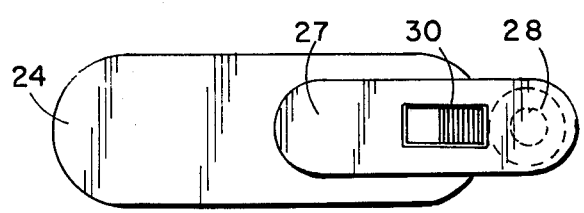

HAND-WARMING AND LIQUID-HEATING DEVICE

BACKGROUND OF THE INVENTION

1. Field of the Invention

The present invention relates to a combination hand-warming and liquid refreshment heating device for outdoor use wherein the liquid can be kept at a plurality of temperatures depending upon the desires of the person utilizing the device.

2. Description of the Prior Art

Catalytic hand warmers have proven most satisfactory to those wishing to have additional sources of warmth outdoors. Such hand warmers are used by hunters and sportsmen who spend a considerable amount of continuous time in winter climates out-of-doors. Some of the prior art in the area of hand warmers, and more particularly catalytic hand warmers, are disclosed in the Smith U.S. Pat. Nos. 2,942,601, the Wilcox U.S. Pat. No. 2,914,060, and the Wintz U.S. Pat. No. 3,405,704. The above patents do not disclose a device for utilizing catalytic hand warmers in a manner that not only warms the body of the individual utilizing the device, but also heats liquid refreshment such as soups, coffee, etc. for consumption outdoors. At present individuals desiring to have hot liquid refreshment must carry a thermos bottle. After these liquids have been consumed, these individuals have no easy means of either reheating the liquid refreshment or heating other liquids. Such individuals are further inconvenienced by having to carry an empty thermos bottle around with them. Therefore it is a primary object of this invention to provide a convenient and easy-to-use catalytic hand warmer having means for heating liquid refreshment included therein.

SUMMARY

The device of this invention is basically a catalytic hand-warming device which further includes a chamber for heating liquid refreshment by means of the catalytic heater and, in one embodiment, can raise the temperature of the liquid to a plurality of temperatures by means of an auxiliary heating unit. It should be noted that an advantage of the present invention is that the heated liquid adds mass to the hand warmer thereby creating a larger hot mass which retains heat for a longer period of time. Further, the introduction of a liquid refreshment chamber makes the catalytic hand warmer more appealing by serving two purposes instead of one.

The device of this invention consists of an apparatus fitting over a catalytic hand warmer base containing a chamber for holding liquid refreshment. At the top of this liquid chamber is an opening through which the liquid can be poured or from which the liquid can be consumed directly. Further included in one embodiment of this invention is an auxiliary heating unit powered by an energy source in association with a thermal breaker so that in addition to having the liquid refreshment heated to the temperature of the catalytic heater, one can energize the auxiliary heating unit to raise the temperature of the liquid to a boil or to a preselected desired temperature.

BRIEF DESCRIPTION OF THE DRAWINGS

FIG. 4 illustrates a perspective side view of the device of this invention utilizing an auxiliary heating source.

FIG. 5 illustrates a top view of the device of this invention utilizing an auxiliary heating source.

FIG. 6 illustrates a perspective side view of the device of this invention utilizing an auxiliary heater with energy source in an alternate position.

FIG. 7 illustrates a top view of the device of this invention utilizing an auxiliary heater with energy source in an alternate position.

FIG. 8 is a perspective view of the device of this invention located above a catalytic heater onto which it will be inserted.

DESCRIPTION OF THE PREFERRED EMBODIMENT

Figure 1:
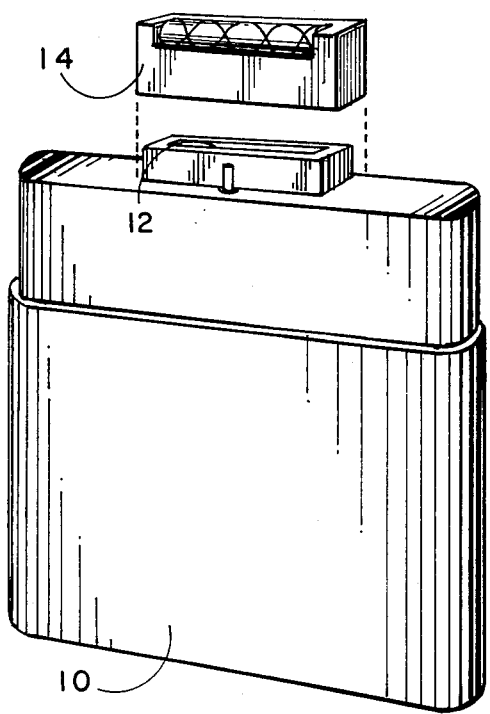
FIG. 1 illustrates a typical catalytic hand warmer with the catalytic converting unit lifted off the fuel reservoir for purposes of illustration.

FIG. 1 illustrates a well-known catalytic hand warmer of the type presently on the market and as described in the patents disclosed in the Description of the Prior Art. Base 10 of the hand-warming unit is oval in general shape and contains an absorbent material such as cotton. Fuel, such as naptha, white gasoline or other fuel recommended by the manufacturer, is poured into opening 12 on top of base 10. Over this opening fits catalytic converter 14 which burns the fuel creating a flameless heat. In practice a cover would fit over catalytic converter 14 so that it will not burn the individual carrying the unit. A plurality of apertures are usually located in this cover to allow air to circulate through the catalytic burner. One of these holes can be large enough to accommodate a cigarette for convenient lighting of same. The usual mode of carrying this catalytic hand warmer is within a flannel pouch either in one's pocket or against one's body while outdoors.

Figure 2:
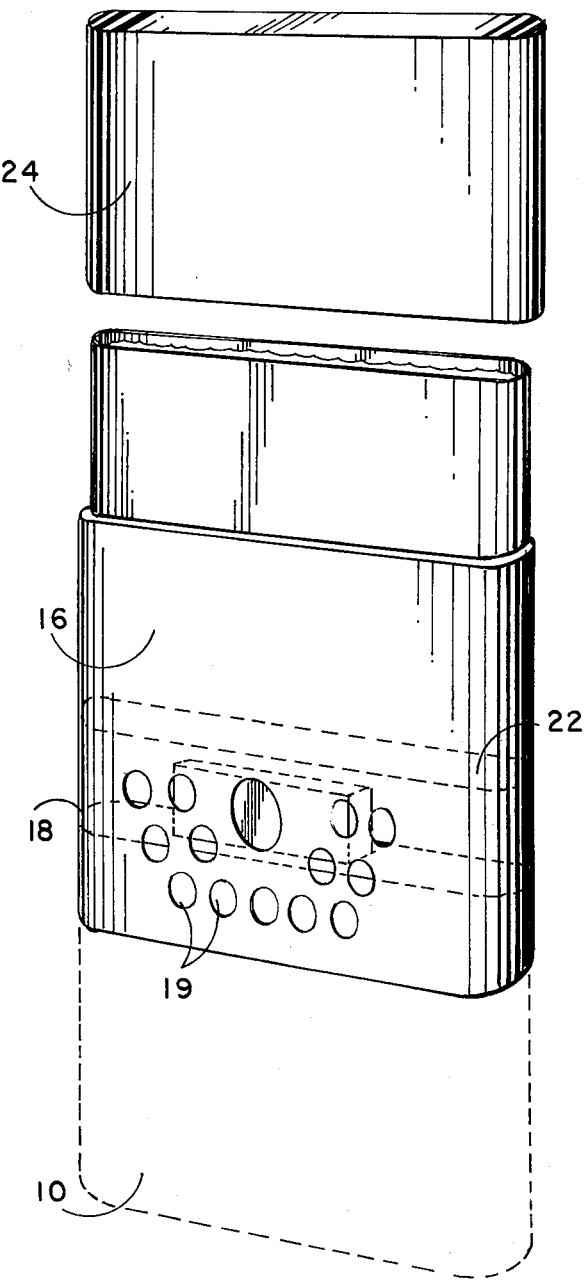
FIG. 2 illustrates a perspective side view of the device of this invention.

A side view of the device of this invention is illustrated in FIG. 2. Liquid chamber 16 having insertion member 18 at its base is inserted over the catalytic burner in place of its standard cover. Insertion member 18 has a plurality of apertures 19 which allow oxygen to reach the catalytic converter. Above the catalytic converter between liquid chamber 16 and insertion member 18 is baffle 22 to prevent the liquid in chamber 16 from coming in contact with the catalytic converter. At the top of the liquid chamber is cover cap 24 which fits securely in a fluid-tight relation. Such chamber can be constructed of anodized aluminum or equivalent. In use, liquid is poured into liquid chamber 16, and cover cap 24 is slid into its closed position. The liquid in the chamber is then heated by the catalytic converter. When one desires to consume the liquid refreshment, one removes cover cap 24 and pours the liquid into a cup, or one can consume the liquid refreshment directly from the top opening of the liquid chamber. Another embodiment of this invention can have the cover cap permanently affixed to the liquid chamber with a removable cap member so that one could obtain the liquid through a smaller opening.

Figure 3:
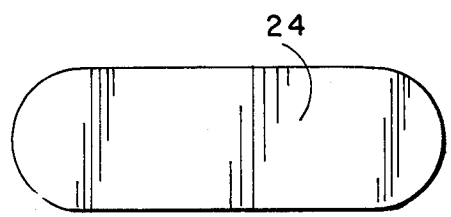
FIG. 3 illustrates a top view of the device of this invention.

FIG. 3 illustrates a top view of the device of this invention as illustrated in FIG. 2 showing cover cap 24.

An embodiment of this invention utilizing an auxiliary heating source is illustrated in FIG. 4 wherein the cover cap 24 has extension compartment 26 thereon containing electrical energy source 28 such as a battery or equivalent. Switch 30 completes a circuit allowing current to flow to heating element 32 which extends within cover cap 24 and would, when the cover cap is placed on the liquid chamber, be immersed in the liquid contained within the liquid chamber. Heating element 32 can be associated with encased thermal breaker 34 which can be pre-set to turn the battery off at a desired temperature. Thus if one wished to have the liquid refreshment warmed to the temperature of the catalytic converter, one would not energize the battery; but if one wished to have a hotter drink, one would turn on switch 30 on top of the energy source to activate the energy source which in turn would power the auxiliary heater to raise the temperature of the liquid to the desired temperature. It should be noted that since the liquid contents are already at the temperature of the catalytic heater, the energy from a small powerful battery would be sufficient to raise the temperature of the liquid contents to the boiling point or other pre-selected temperature.

FIG. 5 illustrates a top view of the device of this invention as seen in FIG. 4 utilizing an auxiliary heating source powered by battery 28 within extension compartment 26.

FIG. 6 illustrates a side view of the device of this invention utilizing an auxiliary heating source in an alternate position from that illustrated in FIGS. 4 and 5. Alternate extension compartment 27 is affixed to the side of cover cap 24 rather than to its top as illustrated in FIGS. 4 and 5. This side positioning of energy source 28 can be more practical when utilized with a larger capacity liquid chamber and heater units which have a wider base than the standard style catalytic heater discussed in the Description of the Prior Art.

FIG. 7 illustrates a top view of the device of this invention utilizing an auxiliary heating source within alternate extension compartment 27 as illustrated in FIG. 6. Also shown are switch 30, cover cap 24 and battery 28.

FIG. 8 is a perspective view of the device of this invention located above a catalytic heater onto which it will be inserted.

It should be noted that the device of this invention can be used in combination with any shaped catalytic-type hand warmer and is not limited to any particular hand warmer. Although the present invention has been described with reference to particular embodiments, it will be apparent to those skilled in the art that variations and modifications can be substituted therefor without departing from the principles and spirit of the invention.

I claim:

1. A hand-warming and liquid-heating unit combination comprising:
 a catalytic hand-warming unit;
 a liquid-containing chamber affixed to said catalytic hand-warming unit;
 an insertion member, having a plurality of apertures for air circulation to a heating element of said hand-warming unit being slideably insertable between and engageable with said hand-warming unit and said liquid-containing chamber;
 a baffle member to enclose and divide said liquid-containing chamber from said hand-warming unit;
 a cover cap slideably insertable over the opening of said liquid-containing chamber in a fluid-tight relationship;
 a heating element associated with said cover cap to protrude within said liquid-containing chamber; and
 an energizing source associated with said heating element compartmentally segregated from said liquid-containing chamber.

2. A device as recited in claim 1 wherein said cover cap includes said energizing source compartment for powering said heating element emanating from said cover cap for heating liquid in said liquid-containing chamber.

3. A device as recited in claim 1 wherein said energizing source for said heating element includes:
 an extension compartment adjacent to said cover cap for containing said energizing source.

4. A device as recited in claim 1 further including means for activating and deactivating said heating element.

5. A device as recited in claim 4 wherein said means for activating and deactivating said heating element comprises a switch.

6. A device as recited in claim 4 wherein said means for activating and deactivating said heating element includes an encased thermal breaker within said liquid compartment for deactivating said heating element once a pre-selected temperature has been reached within said liquid-containing chamber.

7. In a catalytic hand-warming unit and liquid-heating unit combination, the improvement comprising:
 a liquid-containing chamber;
 an insertion member, having a plurality of apertures for air circulation to the heating element of said hand-warming unit, slideably engageable to interpose the base of said liquid container chamber and said hand-warming unit;
 a removable cover cap insertable over an opening of said liquid-containing chamber in a fluid type relationship;
 a heating element associated with said cover cap to protrude within said liquid-containing chamber; and
 an energizing source associated with said heating element, compartmentally segregated from said liquid-containing chamber.

* * * * *